United States Patent [19]

Barbee et al.

[11] Patent Number: 5,338,390
[45] Date of Patent: Aug. 16, 1994

[54] CONTACTLESS REAL-TIME IN-SITU MONITORING OF A CHEMICAL ETCHING PROCESS

[75] Inventors: Steven G. Barbee, Dover Plains; Tony F. Heinz, Chappaqua; Leping Li, New Paltz; Eugene H. Ratzlaff, Hopewell Junction, all of N.Y.

[73] Assignee: International Business Machines Corporation, Armonk, N.Y.

[21] Appl. No.: 985,413

[22] Filed: Dec. 4, 1992

[51] Int. Cl.$^5$ ............................ G01N 27/46; C25F 3/02
[52] U.S. Cl. .................................... 156/627; 204/129.2
[58] Field of Search .................... 156/627; 204/129.2

[56] References Cited

U.S. PATENT DOCUMENTS

| 2,933,675 | 4/1960 | Hoelzle .......................... 156/626 X |
| 4,497,699 | 2/1985 | de Wit et al. ...................... 204/129.2 |
| 4,793,895 | 12/1988 | Kaanta et al. ......................... 156/627 |
| 4,995,939 | 2/1991 | Ferenczi et al. ..................... 156/627 |
| 5,081,421 | 1/1992 | Miller et al. ......................... 324/671 |

FOREIGN PATENT DOCUMENTS 46568  4/1980  Japan .................................. 156/627

OTHER PUBLICATIONS

"Resistance/Capacitance Methods for Determining Oxide Etch End Point" by C. Liu and H. Sauer, IBM Technical Disclosure Bulletin, FI873-0490, vol. 16, No. 8, Jan. 1974.

"Capacitive Etch Rate Monitor for Dielectric Etching" by W. Goubau, IBM Technical Disclosure Bulletin, SA886-0341, vol. 31, No. 1, Jun. 1988.

"Establishing End Point During Delineation Process" by J. Hoekstra, IBM Technical Disclosure Bulletin, YO872-0303, vol. 16, No. 6, Nov. 1973.

"An In-Situ Etch Rate Monitor Controller" by E. Bassous and T. Ning, IBM Technical Disclosure Bulletin, YO377-0116, vol. 20, No. 3, Aug. 1977.

*Primary Examiner*—Thi Dang
*Attorney, Agent, or Firm*—Michael J. Balconi-Lamica

[57] ABSTRACT

A contactless method and apparatus for real-time in-situ monitoring of a chemical etching process for the etching of at least one wafer in a wet chemical etchant bath are disclosed. The method comprises the steps of providing at least two conductive electrodes in the wet chemical bath, said at least two electrodes being proximate to but not in contact with the at least one wafer; and monitoring an electrical characteristic between the at least two electrodes, wherein a prescribed change in the electrical characteristic is indicative of a prescribed condition of the etching process. Such a method and apparatus are particularly useful in a wet chemical etch station.

14 Claims, 2 Drawing Sheets 5,338,390

CONTACTLESS REAL-TIME IN-SITU MONITORING OF A CHEMICAL ETCHING PROCESS

BACKGROUND OF THE INVENTION

1. Field of the Invention

This invention generally relates to a method and apparatus for monitoring the etching condition of a chemical etching process, and more particularly, to a contactless real-time in-situ method and apparatus for the same.

2. Discussion of the Related Art

Etching rates and etch end points must be carefully monitored and controlled in order to end etching processes at the desired time. In semiconductor processing, inadequate or excess etching time can result in undesirable film patterning. For instance, for semiconductor devices having film layers or features in the micron and sub-micron range, an inadequate etch or an excess etch would result in the insufficient removal or the excess removal of a desired layer. Insufficient removal of a desired layer can result in an undesired electrical open or electrical short when the desired layer to be removed is an insulator or a conductor, respectively. Additionally, if the etch is in excess, undercutting or punch through can occur resulting in poorly defined film patterning or total lift-off. Inadequate or excess etching time further leads to undesirable reliability problems in the subsequently fabricated semiconductor device. As a semiconductor wafer is extremely expensive due to many processing steps involved in the making thereof, the need to critically control the etching end point in an etching process is highly desirable.

An etch end point must be accurately predicted and/or detected to terminate etching abruptly. Etch rates, etch times, and etch end points are difficult to consistently predict due to lot-to-lot variations in film thickness and constitution, as well as etch bath temperature, flow, and concentration variability. That is, an etch rate is dependent upon a number of factors, which include, etchant concentration, etchant temperature, film thickness, and the film characteristics. Precise control of any of these factors can be very expensive to implement, for example, concentration control.

Currently, most etch rate end point determination techniques depend on indirect measurement and estimation techniques. Some etch monitoring techniques have relied on external measurements of film thickness followed by etch rate estimation and an extrapolated etch end point prediction. However, etch rates may vary due to batch-to-batch differences in the chemical and physical characteristics of the film or the etchant. These extrapolation methods are inadequate.

Real-time, in-situ monitoring is preferred. Some in-situ techniques monitor the etch rate of a reference thin film. This may require additional preparation of a monitor wafer containing the reference thin film or a suitable reference may be unavailable. Still other techniques require physical contact of electrical leads with the wafer being etched and electrical isolation of those leads and associated areas of the wafer from the etchant. This presents problems associated with contamination, contact reliability and reproducibility, and the physical constraints which affect ease of use in manufacturing or automation.

It would thus be desirable to provide a method and apparatus which provides non-contact, real-time, in-situ monitoring of an etching condition of a wafer being etched.

SUMMARY OF THE INVENTION

An object of the present invention is to overcome the problems in the art discussed above.

Another object of the present invention is to provide a non-contact method of monitoring the etching condition of a wafer being etched.

Yet another object of the present invention is to provide an accurate real-time, in-situ method and apparatus for monitoring an etching condition of a wafer being etched.

According to the present invention, a contactless method for real-time in-situ monitoring of a chemical etching process for the etching of at least one wafer in a wet chemical etchant bath comprises the steps of:

a) providing at least two conductive electrodes in the wet chemical bath, said at least two electrodes being proximate to but not in contact with the at least one wafer; and b) monitoring an electrical characteristic between the at least two electrodes, wherein a prescribed change in the electrical characteristic is indicative of a prescribed condition of the etching process.

In addition, according to the present invention, a contactless real-time in-situ chemical etch monitor for providing an indication of a prescribed condition of an etching process of at least one wafer to be etched in a wet chemical etchant bath comprises at least two conductive electrodes positionable inside the wet chemical etchant bath to be proximate to but not in contact with the at least one wafer to be etched. A monitoring means monitors an electrical characteristic between the at least two electrodes, wherein a prescribed change in the electrical characteristic is indicative of the prescribed condition of the etching process.

BRIEF DESCRIPTION OF THE DRAWINGS

The foregoing and other teachings and advantages of the present invention will become more apparent upon a detailed description of the best mode for carrying out the invention as rendered below. In the description to follow, reference will be made to the accompanying drawings, in which.

DETAILED DESCRIPTION OF THE PREFERRED EMBODIMENTS

Figure 1:
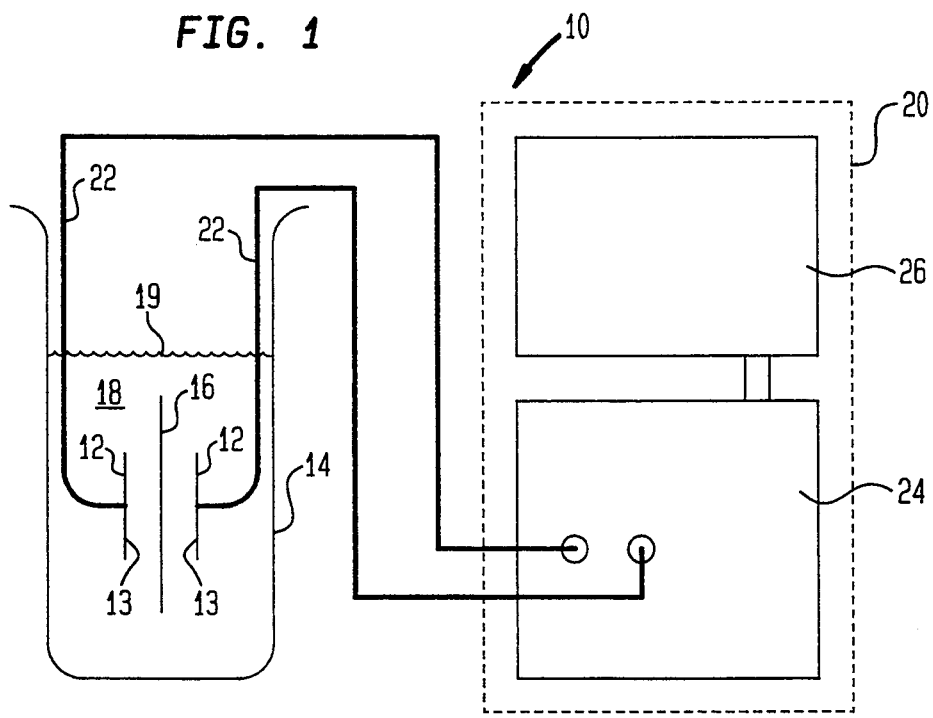
FIG. 1 shows a contactless real-time in-situ etching condition monitor according to the present invention.

Referring now to FIG. 1, there is shown a contactless real-time, in-situ monitor 10 for providing an indication of a prescribed condition in an etching process according to the present invention. Monitor 10 comprises at least two conductive electrodes 12 positionable inside an etchant tank 14. Etchant tank 14 is of an appropriate size for receiving at least one wafer 16 to be etched. The at least one wafer 16 comprises a semiconductor wafer having at least one film layer thereon which is desired to be removed by a chemical etchant bath 18. The at least one wafer 16 is positioned in any suitable standard wafer carrier (not shown) and submerged in the chemical etchant bath 18, wherein the chemical etchant bath comprises a suitable etchant for removing the desired film layer on the at least one wafer 16. While only one wafer is shown, more than one wafer may be placed in the etchant bath 18.

Electrodes 12 can comprise, for example, flat plates, having dimensions of approximately 1 inch square and 0.01 inches thick. Electrodes 12 further comprise a conductive material which is insensitive to the etchant bath 18 and non-contaminating, such as, platinum. Electrodes 12 are positionable within the etchant bath 18 by any suitable means such that the faces 13 of electrodes 12 are oriented perpendicular to the liquid surface 19 of bath 18 and further wherein electrodes 12 are substantially parallel to each other. As shown in FIG. 1, the electrodes 12 are positioned on opposite sides of the at least one wafer 16, wherein wafer 16 is in between the electrodes 12. Furthermore, electrodes 12 are spaced away from the at least one wafer 16 by a prescribed distance, for example, one-quarter of an inch. The prescribed distance is established such that the electrodes 12 are remote from and not in direct contact with the at least one wafer 16, thus eliminating any need for special physical contacting electrodes, while permitting suitable etchant access and flow. The remote and non-contact electrodes 12 further preclude any physical damage to the at least one wafer 16.

Electrodes 12 are connected to an electrical characteristic monitoring device 20 by electrical wires 22. Electrical wires 22 can comprise, for example, 0.020 inch diameter 60/40 platinum/rhodium wire and further be sheathed with an insulating material (not shown). The wires 22 can be rigidly clamped above the etchant bath 18 at opposite sides of the tank 14 and are directed vertically down into the etchant bath 18 along the sides of tank 14 until reaching the approximate vertical center of the solution or etchant bath 18. Immersed in the etchant bath 18, wires 22 contain an approximate bend of 90 degrees and are directed toward the horizontal center of the solution (and each other). Furthermore, wires 22 terminate at the electrodes 12, thereby securing the electrodes 12.

Electrical characteristic monitoring device 20 can comprise, for example, an impedance analyzer 24 and a data recording and displaying device 26, such as any commercially available chart recorder. It should be noted that electrical characteristic monitoring device 20 can likewise comprise an impedance analyzer and a computer or a programmable controller, the computer or programmable controller providing feedback control to initiate, control, and terminate an etching operation. Impedance analyzers, computers, and programmable controllers are well known in the art.

In operation, the present invention provides a real-time method and apparatus for monitoring a prescribed etching characteristic, such as, etch rate or etch end point of an etching process. Etch end point is used herein to refer to the point in time when a desired film layer or portion thereof is completely removed. Monitoring of the prescribed etching characteristic is effected by electrically sensing, in-situ, changes in an electrical characteristic, such as, the impedance or an element or elements of impedance (e.g., reactance and/or resistance), between the two electrodes 12. The electrodes 12 are positioned proximate to but not in contact with the etched wafer 16. During the removal of a conducting or dielectric film from the etched wafer 16, the impedance of the etched wafer 16 and its environment changes. The changes of impedance with time are related to etching rates. Changes in the rate of change in the impedance element(s), specifically slope reversals and trend discontinuities, are related to changes in phase transitions where a change in the etchant-wafer interface has occurred. These impedance transitions mark distinct etching characteristics, such as, etch end points. Thus etching rates and etching end points can be readily determined in real-time.

The contactless real-time, in-situ chemical etching method and apparatus of the present invention operate by first placing the wafer 16 to be etched into the etchant bath 18. Wafer 16 is proximate to but not touching electrodes 12, thus avoiding an unnecessary and potentially damaging contact between the wafer 16 and electrodes 12. Electrodes 12 are used for measuring an impedance such that wafer 16 is subject to an electric field developed between the electrodes 12. The impedance of the electrodes 12 and their environment is measured in a standard way for measuring impedance, such as by applying DC, AC, or pulsed current or voltage to the electrodes and monitoring the passed current or developed potential. Electrical characteristic monitoring means 20 provides a means for monitoring the passed current or developed potential in an appropriate way. As previously discussed, electrical characteristic monitoring means 20 can comprise, for example, any commercially available impedance analyzer or conductivity bridge.

Described in another way, the present invention provides for the in-situ monitoring of dimensional changes of the wafer in the liquid etchant. Dimensional changes, such as film thinning, are monitored by sensing resultant changes in the electrical characteristics of the wafer and the etchant environment. The at least two electrodes 12 are proximate to but not in direct physical contact with the at least one wafer 16. The electrodes 12 and wafer 16 are in ohmic or capacitive contact with the etchant solution 18. Electrical characteristic monitoring means 20 provides a means of monitoring changes in impedance or changes in an appropriate element of the impedance between the electrodes.

EXAMPLE

Operation of the present invention will now be further described using an example. The present invention has been applied to the monitoring of the etching of a blanket silicon oxide film layer from each of several silicon wafers in a dilute aqueous hydrofluoric (HF) acid etch bath. The present invention provided sufficient information to accurately identify an etch end point, that is, where the etchant had removed the oxide layer.

Etching was performed using an etchant bath 18 comprising 2.7% HF, filled to about 6 inches deep contained in tank 14. The bath 18 was stirred via a conventional teflon-coated magnetic stirring bar about 1 inch long, rotating at about 4 Hz. All measurements were made at ambient room temperature.

A wafer 16 comprising a silicon wafer of approximately 0.1 ohm cm resistivity, 3 inch diameter, backside rough, with a blanket silicon oxide approximately 5000 Angstroms thick thereon, was etched in the etchant bath 18 of 2.7% HF. Wafer 16 was held at an edge portion thereof by a small nylon vise (not shown) attached to the end of a stainless-steel rod (not shown). The wafer was then fully immersed and rigidly clamped in the center of the tank 14 with the wafer face perpendicular to the surface 19 of the etchant bath 18.

Figure 2:
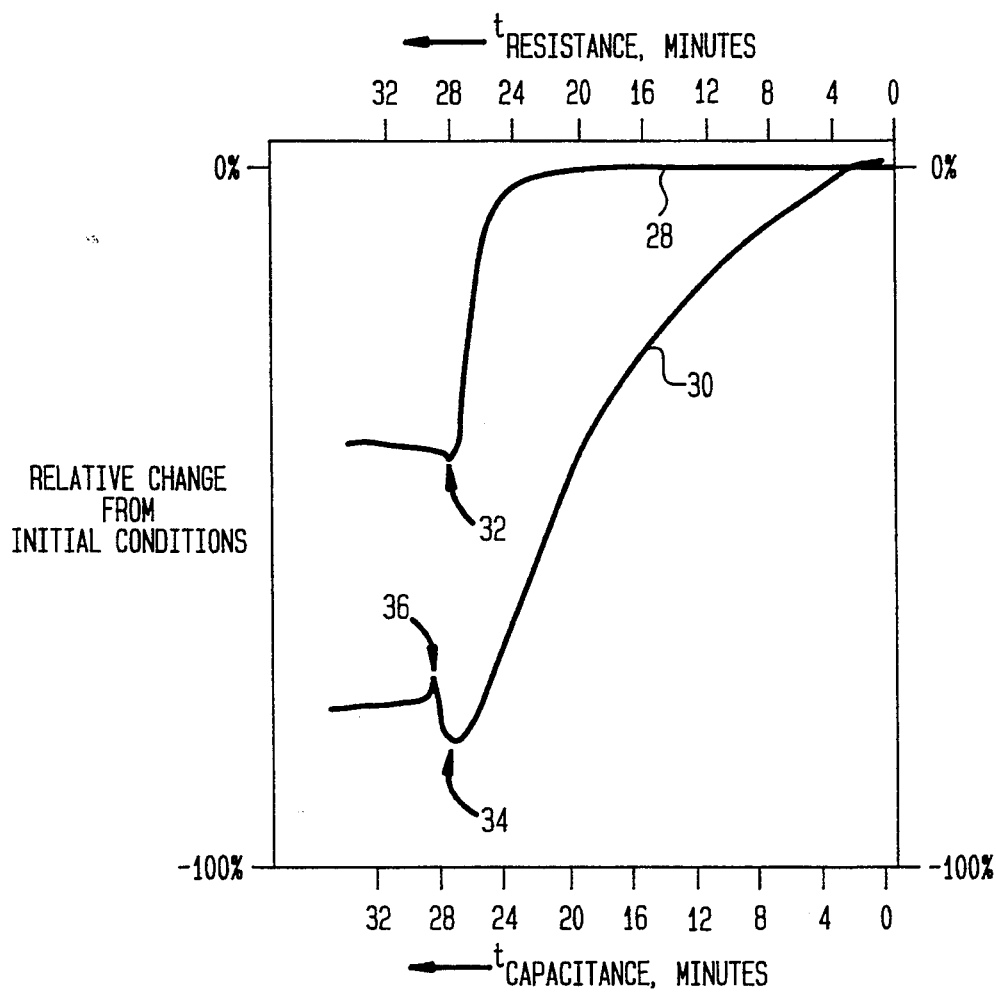
FIG. 2 shows a graph of monitored electrical characteristics according to the present invention; and, FIG. 3 shows an etch station incorporating the contactless real-time in-situ etching condition monitor according to the present invention.

Upon the submersion of the wafer 16 into the bath 18, electrical characteristics comprising resistance and capacitance were monitored simultaneously in real-time using impedance analyzer 24 with an excitation oscillator frequency of 10 KHz. Changes in resistance and capacitance with time were recorded by chart recorder 26 and are shown in FIG. 2 by curves 28 and 30, respectively. The etch was complete in approximately 29 minutes.

As shown in FIG. 2, the resistance record 28 is marked by negligible change during the first 22 minutes followed by an exponential decrease (increasingly negative slope with time) before the occurrence of an etching end point indicated by the numeral 32. This is followed abruptly by a reversal to a slightly (about 1-2%) higher resistance and then a nearly constant, limiting steady-state resistance. The overall change is on the order of 50% of the resistance observed just after the wafer 16 is inserted in the bath 18.

The capacitance record 30 decreases in a slightly accelerating fashion for the first 25 minutes. This acceleration slows and then quickly reverses during the last 2 ½ minutes, reaching a minimum capacitance (indicated by numeral 34) of about 10% of the starting value before increasing abruptly about 10%. This is followed by another abrupt change (indicated by numeral 36) being an abrupt reversal in capacitance of about 5% to a lower capacitance and then to a nearly constant, limiting, steady-state capacitance. The abrupt reversal indicated by numeral 36 occurs simultaneously with the abrupt change indicated by numeral 32 observed in the resistance characteristic at the end point. (Note that the time scales of resistance and capacitance are offset slightly.) The final capacitance was measured to be about 15% of the starting value.

Figure 3:
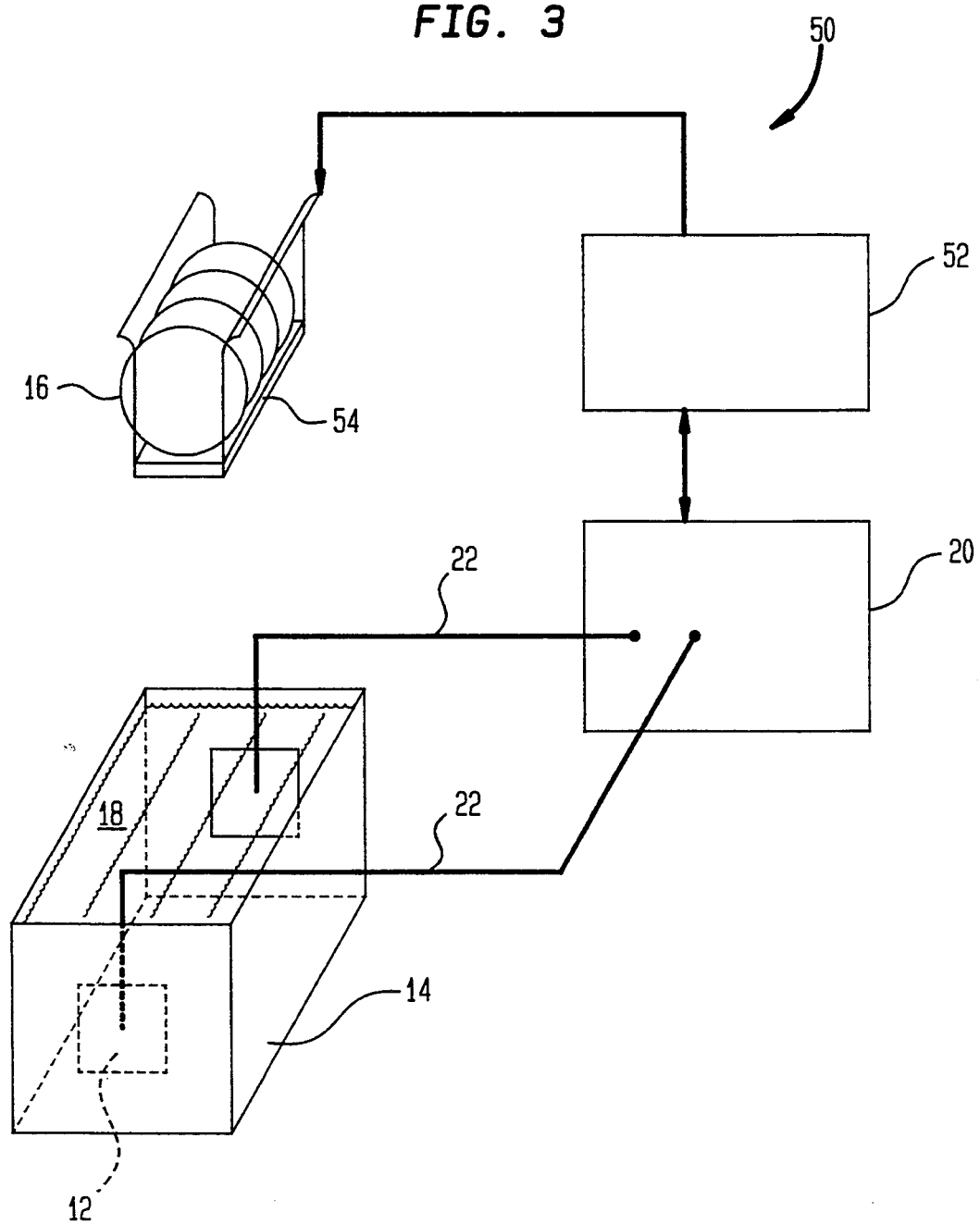

Referring now to FIG. 3, in an alternate embodiment of the present invention, an etch station 50 incorporating the contactless real-time in-situ monitor of the present invention includes a control means 52 which is responsive to electrical characteristic monitoring means 20. Control means 52 can comprise, for example, a computer or programmable controller in conjunction with any suitable mechanism (not shown) for raising and lowering the wafer carrier 54 into and out of the bath 18. Means 52 controls the placement of the wafer carrier 54 into and out of the etchant bath 18 in response to the sensing of a prescribed etching condition or conditions by the electrical characteristic monitoring means 20. Thus, etch station 50 provides accurate and highly efficient etching control.

Thus there has been shown a real-time in-situ monitoring method and apparatus which provide accurate, non-contact, monitoring of an etching characteristic of an etching process. Such a method and apparatus are inexpensive to implement and ensure the integrity of the etched wafer or wafers. Etching of a wafer can be controlled precisely.

While the invention has been particularly shown and described with reference to the preferred embodiment thereof, it will be understood by those skilled in the art that various changes in form and detail may be made therein without departing from the spirit and scope of the invention. For example, while the invention has been described with respect to the detection of an etching end point of a blanket wafer having a silicon oxide film layer thereon, other wafers (e.g., blanket or patterned) may be used. System condition parameters, such as impedance analyzer frequency, etc., may need to be adjusted accordingly to obtain optimum detection sensitivity.

What is claimed is:

1. A contactless method for real-time in-situ monitoring of a chemical etching process during etching of at least one wafer in a wet chemical etchant bath, said method comprising the steps of:
   a) providing two conductive electrodes in the wet chemical bath, the two electrodes being proximate to but not in contact with the at lest one wafer and further wherein each of the electrodes is positioned on an opposite side of the at least one wafer; and
   b) monitoring an impedance between the two electrodes, wherein a prescribed change in the impedance is indicative of a prescribed condition of the etching process.

2. A contactless method for real-time in-situ monitoring of a chemical etching process during etching of at least one wafer in a wet chemical etchant bath, said method comprising the steps of:
   a) providing at least two conductive electrodes in the wet chemical bath, the at least two electrodes being proximate to but not in contact with the at least one wafer; and
   b) monitoring an electrical characteristic between the at least two electrodes, wherein a prescribed change in the electrical characteristic is indicative of a prescribed condition of the etching process, wherein the monitoring of an electrical characteristic comprises monitoring impedance and further wherein the prescribed change comprises a prescribed change in impedance.

3. The method of claim 1, wherein the prescribed condition in step b) comprises an etching end point.

4. A contactless method for real-time in-situ monitoring of a chemical etching process during etching of at least one wafer in a wet chemical etchant bath, said method comprising the steps of:
   a) providing at least two conductive electrodes in the wet chemical bath, the at least two electrodes being proximate to but not in contact with the at least one wafer, wherein the at least two electrodes comprise two electrodes and further wherein each of the electrodes is positioned on an opposite side of the at least one wafer; and
   b) monitoring an electrical characteristic between the at least two electrodes, wherein a prescribed change in the electrical characteristic is indicative of a prescribed condition of the etching process.

5. A contactless real-time in-situ chemical etch monitor for providing an indication of a prescribed condition of an etching process during etching of at least one wafer in a wet chemical etchant bath, said monitor comprising:
   a) at lest two conductive electrodes, wherein said at least two electrodes comprise two electrodes;
   b) means for positioning said at least two conductive electrodes inside the wet chemical etchant bath to be proximate to but not in contact with the at least one wafer and further wherein each of the electrodes is positioned on an opposite side of the at least on wafer; and
   c) means for monitoring an impedance between said at least two electrodes, wherein a prescribed change in the impedance is indicative of the prescribed condition of the etching process.

6. A contactless real-time in-situ chemical etch monitor for providing an indication of a prescribed condition of an etching process during etching of at least one wafer in a wet chemical etchant bath, said monitor comprising:
   a) at least two conductive electrodes;
   b) means for positioning said at least two conductive electrodes inside the wet chemical etchant bath to be proximate to but not in contact with the at least one wafer; and
   c) means for monitoring an electrical characteristic between said at least two electrodes, wherein a prescribed change in the electrical characteristic is indicative of the prescribed condition of the etching process, wherein said monitoring means comprises means for monitoring an impedance and further wherein the prescribed change comprises a prescribed change in impedance.

7. A contactless real-time in-situ chemical etch monitor for providing an indication of a prescribed condition of an etching process during etching of at least one wafer in a wet chemical etchant bath, said monitor comprising:
   a) at least two conductive electrodes, wherein said at least two electrodes comprise two electrodes;
   b) means for positioning said at least two electrodes inside the wet chemical etchant bath to be proximate to but not in contact with the at least one wafer and further wherein each of the electrodes is positioned on an opposite side of the at least one wafer; and
   c) means for monitoring an electrical characteristic between said at least two electrodes, wherein a prescribed change in the electrical characteristic is indicative of the prescribed condition of the etching process.

8. A contactless method for real-time in-situ control of an etching process during etching of at least one wafer in an etch station, the etch station having a wet chemical etchant bath, said method comprising the steps of:
   a) providing two conductive electrodes in the wet chemical bath, the two electrodes being proximate to but not in contact with the at least one wafer, and further wherein each of the electrodes is positioned on an opposite side of the at least one wafer;
   b) monitoring an impedance between the two electrodes, wherein a prescribed change in the impedance is indicative of a prescribed condition of the etching process; and
   c) controlling the etching process in response to the monitoring of the prescribed change in the impedance.

9. A contactless method for real-time in-situ control of an etching process during etching of at least one wafer in an etch station, the etch station having a wet chemical etchant bath, said method comprising the steps of:
   a) providing at least two conductive electrodes in the wet chemical bath, the at least two electrodes being proximate to but not in contact with the at least one wafer;
   b) monitoring an electrical characteristic between the at least two electrodes, wherein a prescribed change in the electrical characteristic is indicative of a prescribed condition of the etching process, wherein monitoring of an electrical characteristic comprises monitoring impedance and further wherein the prescribed change comprises a prescribed change in impedance; and
   c) controlling the etching process in response to the monitoring of the prescribed change in the electrical characteristic.

10. The method of claim 8, wherein the prescribed condition in step b) comprises an etching end point.

11. A contactless method for real-time in-situ control of an etching process during etching of at least one wafer in an etch station, the etch station having a wet chemical etchant bath, said method comprising the steps of:
    a) providing at least two conductive electrodes in the wet chemical bath, the at least two electrodes being proximate to but not in contact with the at least one wafer, wherein the at least two electrodes comprise two electrodes and further wherein each of the electrodes is positioned on an opposite side of the at least one wafer;
    b) monitoring an electrical characteristic between the at least two electrodes, wherein a prescribed change in the electrical characteristic is indicative of a prescribed condition of the etching process; and
    c) controlling the etching process in response to the monitoring of the prescribed change in the electrical characteristic.

12. An etch station having contactless real-time in-situ control of an etching process during etching of at least one wafer in a wet chemical etchant bath, said etch station comprising:
    a) at least two conductive electrodes, wherein said at least two electrodes comprise two electrodes;
    b) means for positioning said at least two conductive electrodes inside the wet chemical etchant bath to be proximate to but not in contact with the at least one wafer and further wherein each of the electrodes is positioned on an opposite side of the at least one wafer;
    c) means for monitoring an impedance between said at least two electrodes, wherein a prescribed change in the impedance is indicative of a prescribed condition of the etching process; and
    d) means for controlling the etching process in response to the monitoring of the prescribed change in the impedance.

13. An etch station having contactless real-time in-situ control of an etching process during etching of at least one wafer in a wet chemical etchant bath, said etch station comprising:
    a) at least two conductive electrodes;
    b) means for positioning said at least two conductive electrodes inside the wet chemical etchant bath to be proximate to but not in contact with the at least one wafer;
    c) means for monitoring an electrical characteristic between said at least two electrodes, wherein a prescribed change in the electrical characteristic is indicative of a prescribed condition of the etching process, wherein said monitoring means comprises means for monitoring an impedance and further wherein the prescribed change comprises a prescribed change in impedance; and
    d) means for controlling the etching process in response to the monitoring of the prescribed change in the electrical characteristic.

14. An etch station having contactless real-time in-situ control of an etching process during etching of at least one wafer in a wet chemical etchant bath, said etch station comprising:

a) at least tow conductive electrodes, wherein said at least two electrodes comprise two electrodes;

b) means for positioning said at least two conductive electrodes inside the wet chemical etchant bath to be proximate to but not in contact with the at least one wafer and further wherein each of the electrodes is positioned on an opposite side of the at least one wafer;

c) means for monitoring an electrical characteristic between said at least two electrodes, wherein a prescribed change in the electrical characteristic is indicative of a prescribed condition of the etching process; and d) means for controlling the etching process in response to the monitoring of the prescribed change in the electrical characteristic.

* * * * *

UNITED STATES PATENT AND TRADEMARK OFFICE
CERTIFICATE OF CORRECTION

PATENT NO. : 5,338,390
DATED : August 16, 1994
INVENTOR(S) : Steven G. Barbee, Tony F. Heinz, Leping Li, Eugene H. Ratzlaff It is certified that error appears in the above-identified patent and that said Letters Patent is hereby corrected as shown below:

In column 6, line 12: change "lest" to --least--.

In column 6, line 57: change "lest" to --least--.

In column 6, line 64: change "on" to --one--

In column 9, line 4: change "tow" to --two--.

Signed and Sealed this

Eighth Day of November, 1994

Attest:

BRUCE LEHMAN

Attesting Officer  Commissioner of Patents and Trademarks